(12) United States Patent
Janik

(10) Patent No.: US 7,433,056 B1
(45) Date of Patent: Oct. 7, 2008

(54) SCATTEROMETRY METROLOGY USING INELASTIC SCATTERING

(75) Inventor: Gary R. Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 434 days.

(21) Appl. No.: 11/182,171

(22) Filed: Jul. 15, 2005

(51) Int. Cl.
*G01B 11/24* (2006.01)
*G01B 11/30* (2006.01)
*G01B 11/14* (2006.01)
*G01J 3/44* (2006.01)
*G01J 3/42* (2006.01)
*G01J 3/427* (2006.01)
*G01J 3/28* (2006.01)

(52) U.S. Cl. .................. 356/601; 356/301; 356/319; 356/326; 356/625

(58) Field of Classification Search .................. None
See application file for complete search history.

(56) References Cited

U.S. PATENT DOCUMENTS 6,067,154 A * 5/2000 Hossain et al. ............ 356/237.2
6,545,755 B1 * 4/2003 Ishihama et al. ............ 356/301
6,924,893 B2 * 8/2005 Oldenbourg et al. ........ 356/369

* cited by examiner

*Primary Examiner*—Gregory J. Toatley, Jr.
*Assistant Examiner*—Gordon J Stock, Jr.
(74) *Attorney, Agent, or Firm*—Bever, Hoffman & Harms, LLP; Jeanette S. Harms

(57) ABSTRACT

A system for characterizing material properties in miniature semiconductor structures performs a scatterometry analysis on inelastically scattered light. The system can include a narrowband probe beam generator and a detector. A single wavelength probe beam from the narrowband probe beam generator produces scattered light from a measurement pattern on a test sample. The scattered light is measured by the detector, and the measurement data (e.g., Raman spectrum) is used in a scatterometry analysis to determine material properties for the measurement pattern. The detector can measure either incoherent inelastically scattered light (e.g., using a spectrometer) or coherent inelastically scattered light (e.g., using an array detector). If the measurement pattern dimensions are substantially similar to actual device dimensions, the material property distributions determined for the measurement pattern can be applied to the actual devices on the test sample.

20 Claims, 7 Drawing Sheets

SCATTEROMETRY METROLOGY USING INELASTIC SCATTERING

BACKGROUND OF THE INVENTION

1. Field of the Invention

The invention relates to the field of metrology, and in particular, to a system and method for accurately and efficiently measuring semiconductor structure characteristics.

2. Related Art

Integrated circuit (IC) device geometries continue to shrink with each generation of process technology. Those size reductions provide significant efficiency and performance benefits in modern ICs. At the same time, the production of such ICs requires increasingly sophisticated and precise manufacturing processes, which in turn requires that highly sensitive metrology techniques and tools be used to ensure proper manufacturing results. Currently, one of the most effective metrology techniques for modern ICs is scatterometry, in which light scattered from a pattern on a wafer is used to determine physical characteristics for structures formed on that wafer. The two main methods of performing scatterometry are spectroscopic scatterometry and single wavelength scatterometry.

FIG. 1A shows a spectroscopic scatterometry system 100A for performing metrology on a test sample 190A. Spectroscopic scatterometry system 100A includes a broadband light source 110A, focusing optics 120A, a stage 130A for supporting test sample 190A, an order blocking aperture 135A, analyzing optics 140A, a spectrometer 145A, and an array detector 150A. To perform a scatterometry measurement, light source 110A generates a broadband probe beam 111A (i.e., a light beam that includes a wide range of wavelengths, such: as a white light), which focusing optics 120A directs onto a measurement pattern 191A on test sample 190A. Note that in some spectroscopic scatterometry systems, focusing optics 120A (and analyzing optics 140A) can include polarizing elements to enable ellipsometric analyses to be performed on the scattered light. Note further that, unlike most optical metrology tools, scatterometry tools such as system 100A generally require a physical pattern on the test sample being measured, so that sufficient light scattering (which is generally due to diffraction effects in the test pattern) occurs.

The scattered light 112A created by diffraction at test sample 190A is composed of a plurality of output beam components called orders, each with its own direction of propagation. Each of the diffraction orders has its own polar angle (angle with respect to wafer normal) and its own azimuthal angle (angle with respect to the projection of the probe beam 111A in the plane of the wafer). There is usually a component emitted with a polar angle equal to the polar angle (angle of incidence) of the probe beam 111A and with an azimuthal angle relative to probe beam 111A of 180 degrees. This component (identified in FIG. 1A as zeroth order beam 112A(0)) is defined as the zeroth diffraction order and corresponds to the reflected beam from an unpatterned sample. The presence of measurement pattern 191A creates other diffraction orders (e.g., negative first order beam 112A(−1) and first order beam 112A(+1)) with other polar angles, both greater than and smaller than the zeroth polar angle. If pattern 191A is one-dimensional and if the projection of the probe beam 111A onto the wafer is aligned with a symmetry axis of pattern 191A, all diffraction orders will have an azimuthal angle of 180 degrees relative to probe beam 111A. Otherwise, orders with other azimuthal angles may also be present. This asymmetric situation is called conical diffraction. In general, the polar (and in some cases azimuthal) angles for all diffraction orders other than the zeroth order depend on wavelength. Therefore all diffraction orders other than the zeroth order are not narrow beams, but instead include a variety of components having various polar and azimuthal angles.

A portion of the scattered light 112A generated in response to broadband light beam 111A is collected by analyzing optics 140A. Often only the zeroth order light is collected (e.g., beam 112A(0)), but other orders may also be collected. Zeroth order beam 112A(0) is selected by order blocking aperture 135A, and then passes through analyzing optics 140A, after which it is dispersed by spectrometer 145A onto array detector 150A. Array detector 150A measures a broadband spectrum of intensities for the various wavelengths of light making up broadband light beam 111A. This output spectrum provides a "pattern signature" that is representative of the particular dimensional characteristics of measurement pattern 191A (e.g., dimensions, composition, and surface roughness). By analyzing the broadband spectrum (or spectra) measured by array detector 150A in conjunction with mathematical modeling of measurement pattern 191A, the desired physical characteristic information of measurement pattern 191A can be determined, even if those physical dimensions are smaller than the wavelengths of light in broadband light beam 111A.

FIG. 1B shows a single wavelength scatterometry system 100B for performing metrology on a test sample 190B. Spectroscopic scatterometry system 100B includes a narrowband light source 110B, focusing optics 120B, a stage 130B for supporting test sample 190B, analyzing optics 140B, and an array detector 150B. To perform a scatterometry measurement, light source 110B generates a narrowband light beam 111B (i.e., a light beam that includes a single wavelength, such as a laser light), which focusing optics 120B directs onto a measurement pattern 191B on test sample 190B. As described with respect to scatterometry system 100A shown in FIG. 1A, focusing optics 120B (and analyzing optics 140B) can include polarizing elements to enable ellipsometric analyses to be performed on the scattered light 112B that is scattered from measurement pattern 191B in response to light beam 111B.

The scattered light 112B is directed by analyzing optics 140B onto array detector 150B, which measures the intensity and directions of the light scattering from measurement pattern 191B. In this case the various diffraction orders making up scattered light 112B (e.g., first order beam 112B(+1), zeroth order beam 112B(0), and negative first order beam 112B(−1)) are all narrowband beams and each has a unique polar and azimuthal angle because there is only a narrow range of wavelengths present in narrowband probe beam 111B. Array sensor 150B measures the intensity and positions of some fraction of the diffraction orders. Knowing the position on the array sensor, combined with the properties of analyzing optics 140B, it is possible to extract the polar and azimuthal angle of each detected diffraction order. The arrangement of diffraction orders, their individual intensities, their polarization properties, and their polar and azimuthal angles depend on the properties of pattern 191B and therefore constitute a "pattern signature" for pattern 191B. This pattern signature can be used with mathematical modeling to extract dimensional and other parameters of pattern 191B.

It is possible to extract even more information about the measurement pattern with either the spectroscopic or narrow band systems by measuring with probe beams of different angles. The angles and spectra of the various diffraction orders depend on both the polar angle and azimuthal angle of the probe beam. For instance, it is possible to measure at different probe azimuthal angles by rotating the wafer in its own plane by means of a rotational mechanism incorporated into stage 190A (shown in FIG. 1A) or 190B (shown in FIG. 1B). Measurements can be taken at two or more angles in sequence, rotating the wafer to the desired azimuthal angle before each measurement. In this case the rest of the measurement system can remain stationary. Measurements can also be made at multiple polar angles, but this requires moving at least one or more of the modules of the measurement system.

In all these scatterometry systems, the scattered light has the same wavelength as the probe light. In the spectroscopic systems each wavelength component of the scattered light is created by exactly the same wavelength component of the probe light. In the narrow-band system all of the scattered light is in the same narrow wavelength range of the probe light. The equality of scattered and probe wavelengths is called elastic scattering, due to the fact that the scattered photons have the same energy as the probe photons and no energy is gained or lost to the sample.

Thus, scatterometry (both spectroscopic scatterometry and single wavelength scatterometry) provides metrology capabilities that typically exceed the capabilities of most other non-destructive measurement techniques, and accordingly is the technique of choice for measuring the extremely small semiconductor structures in advanced ICs. However, as scaling of semiconductor devices extends further into the sub-micron range, material properties (i.e., material characteristics other than dimension) such as stress, strain, embedded charge, composition, and degree of crystallinity become increasingly important.

For example, material stress plays a significant role in the performance of the miniature transistors used in advanced ICs. Because material stress is affected by structure size, the stress within, for example, the active region of a MOS transistor cannot be determined from a stress measurement on a bulk region of a wafer. Unfortunately, conventional stress measurement techniques are mainly directed toward bulk measurements (e.g., the measurement of stress within a film formed over an entire wafer), and are therefore not effective for device-level measurements. For example, Raman spectroscopy is one conventional stress measurement technique for measuring stress in silicon (Si) and silicon germanium (SiGe) structures on semiconductor wafers. Raman scattered light usually is composed of several discrete narrow wavelength output beam components, shifted both above and below the incident narrow wavelength range. The magnitude of the wavelength shift of the highest intensity shifted component is determined by the stress level in the silicon. In a silicon germanium structure the shift of this highest intensity shifted component is determined by both the stress within the silicon germanium and the particular silicon germanium composition (other output beam components exhibit intensities and wavelength shifts that are mainly affected by silicon germanium composition). Therefore, the measured shifts and intensities of the various output beam components can be used to determine the stress and composition of Si and SiGe. A similar process can be used to measure other crystalline and polycrystalline materials. Raman spectroscopy has been combined with high resolution microscopy to make measurements with a spatial resolution down to about 0.5 um. However, this level of spatial resolution is not sufficient for making measurements on advanced semiconductor structures that have dimensions of less than 500 nm.

Accordingly, it is desirable to provide a method and system for measuring material properties in miniature devices and structures.

SUMMARY OF THE INVENTION

The characterization of material properties in modern advanced ICs is becoming increasingly important due to the significant effects such material properties have on device performance. Unfortunately, conventional metrology techniques are typically limited to measurements on structures having dimensions much greater than the wavelength of light used in a probe beam, and are therefore not well suited to measure material properties in actual device structures. To overcome this limitation of conventional metrology techniques, a metrology method and system can measure light scattered inelastically (i.e., light scattered with a different wavelength than the incident light) from a measurement pattern. By applying scatterometry techniques in analyzing the inelastically scattered light, material property data can be determined for the structures making up the measurement pattern, even if the pattern structure dimensions are smaller than the wavelength of the probe beam. In addition, by sizing the pattern structures to be dimensionally similar to actual device structures, the material property data determined for the pattern structures can be applicable to the actual device structures.

In one embodiment, a metrology system can include a beam generator for directing a narrowband probe beam (e.g. a laser or a broadband light source limited to a single wavelength by a monochromator) at a measurement pattern on a test sample and a sensor for measuring inelastic scattering data (e.g., Raman spectra) for light scattered from the measurement pattern in response to the narrowband probe beam. Scatterometry analysis logic (either external to or incorporated into the metrology system) can then process the inelastic scattering data measured by the sensor to determine material property distribution(s) within the measurement pattern.

In various embodiments, the metrology system can include input optics for directing the narrowband probe beam at the measurement pattern, a blocking filter for filtering scattered light having the same wavelength as the narrowband probe beam, output optics for directing the inelastically scattered light onto the sensor (which can include a spectrometer and/or array detector, among other types of sensors), and/or adjustment mechanism(s) for changing the polar and/or azimuthal angle between the narrowband probe beam and the test sample pattern. In another embodiment, the beam generator can include capabilities for adjusting the wavelength of the narrowband probe beam and the blocking filter in the analyzing optics. In another embodiment, the metrology system can include additional means for performing standard scatterometry to determine dimensional characteristics of the measurement pattern that can be used in the analysis of the inelastic scattering data.

In another embodiment, a method for analyzing a test sample can include generating inelastic scattered light from a measurement pattern on the test sample, measuring the inelastically scattered light, and analyzing the measured data (e.g., Raman spectrum) to determine a material property distribution in the measurement pattern. In one embodiment, multiple sets of inelastic scattering data can be generated by varying the polar angle, the azimuthal angle, and/or the wavelength of the narrowband probe beam used to generate the (either incoherent or coherent) inelastically scattered light. In one embodiment, the analysis of the inelastic scattering data can involve generating trial (expected) inelastic scattering data based on a trial distribution(s) for the material property (properties) and a mathematical model for the measurement pattern, comparing the trial inelastic scattering data to the measured inelastic scattering data, and adjusting the trial distribution(s) until the trial inelastic scattering data matches the measured inelastic scattering data. In another embodiment, a standard scatterometry operation can be performed on the measurement pattern to determine physical characteristics (i.e., dimensional characteristics) of the measurement pattern that can be used in the generation of the mathematical model.

The invention will be more fully understood in view of the following description and drawings.

DETAILED DESCRIPTION

The characterization of material properties in modern advanced ICs is becoming increasingly important due to the significant effects such material properties have on device performance. Unfortunately, conventional metrology techniques are typically limited to measurements on structures having dimensions much greater than the wavelength of light used in a probe beam, and are therefore not well suited to measure material properties in actual device structures. To overcome this limitation of conventional metrology techniques, a metrology method and system can measure light scattered inelastically (i.e., light scattered with a different wavelength than the incident light) from a measurement pattern. By applying scatterometry techniques in analyzing the inelastically scattered light, material property data can be determined for the structures making up the measurement pattern, even if the pattern structure dimensions are smaller than the wavelength of the probe beam. In addition, by sizing the pattern structures to be dimensionally similar to actual device structures, the material property data determined for the pattern structures can be applicable to the actual device structures.

As noted above, Raman spectroscopy is sometimes used to measure stress in silicon or silicon germanium device structures. Raman scattered light is a type of inelastically scattered light that is incoherent and has no fixed phase relation to the probe light. Incoherent inelastically scattered light exhibits no diffraction and no discrete scattered beams or orders. Therefore, Raman scattered light is diffuse and is emitted in all directions with a smooth variation in intensity versus direction. The scattering is generally weak and it is preferable to use a high N.A. objective in the analyzing optics to collect as much scattered light as possible.

Figure 1A:
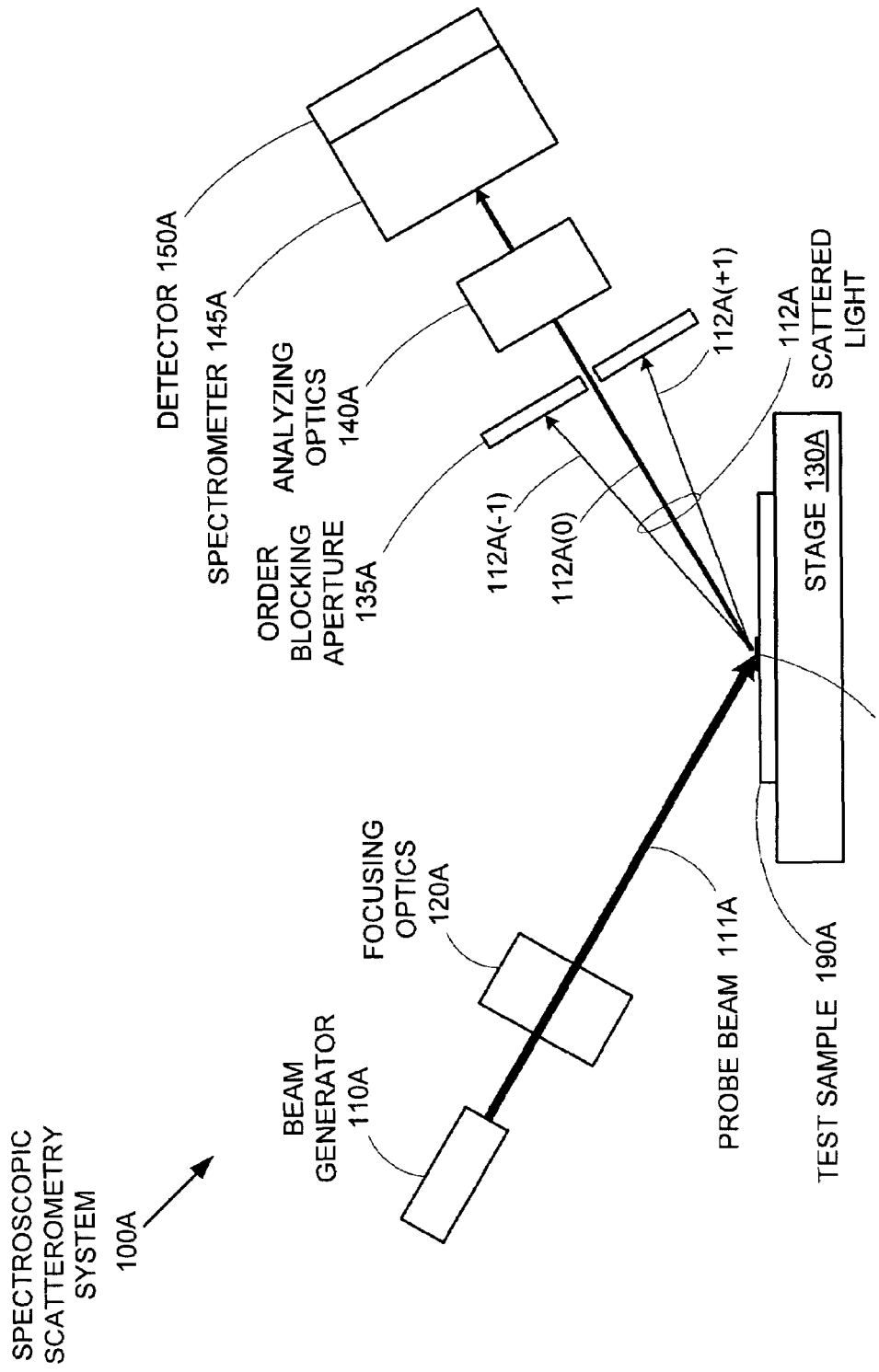
FIGS. 1A and 1B are diagrams of conventional scatterometry systems.
Figure 2A:
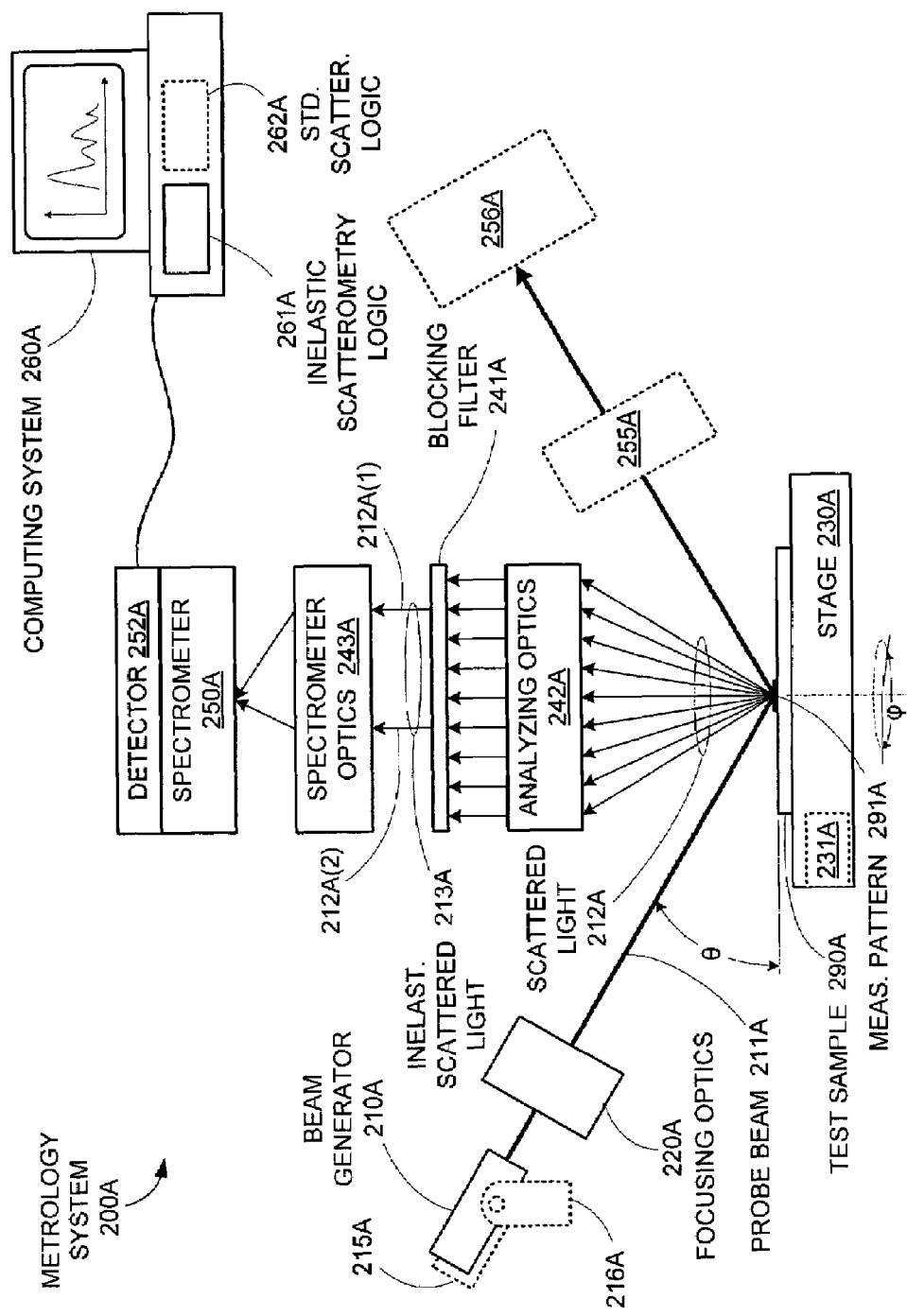
FIGS. 2A and 2B are diagrams of a metrology system based on incoherent inelastic scattering from a measurement pattern.

FIG. 2A shows a metrology system 200A that incorporates incoherent inelastic scattering analysis capabilities in accordance with an embodiment of the invention. Metrology system 200A includes a beam generator 210A, focusing optics 220A, a stage 230A for supporting a test sample 290A, a blocking filter 241A, analyzing optics 242A, spectrometer optics 243A, a spectrometer 250A, and an array detector 252A. A computing system 260A (described in greater detail below) can be coupled to (e.g., via a data cable or network) or incorporated into metrology system 200A to perform analysis on the data gathered by array detector 252A. In various embodiments, metrology system 200A can also include multiple sensors and/or optics to provide additional metrology capabilities, as indicated by optional optics 255A and sensor 256A. Sensor 256A can represent any type and number of detection elements, such as additional spectrometer/detector combinations, intensity detectors, and/or array detectors, among others. For example, in one embodiment, sensor 255 256A could be an array detector, thereby providing metrology system 200 with standard scatterometry capabilities (e.g., as described with respect to FIGS. 1A and/or 1B).

To perform a scatterometry operation, beam generator 210A generates a probe beam 211A that is directed onto a measurement pattern 291A on test sample 290A by focusing optics 220A. Ideally, the structures within measurement pattern 291A will be dimensionally similar to actual devices in test sample 290A (i.e., same size structures with the same or possibly larger spacing), thereby allowing the measurement results generated by metrology system 200A to be applicable to the actual devices in test sample 290A. Probe beam 211A is a narrowband beam of light, i.e., a beam of light having a single wavelength. In one embodiment, beam generator 210A could supply probe beam 211A as a broadband beam (i.e., multi-wavelength beam), and focusing optics 220A could include a monochromator to ensure that only a single wavelength of light reaches test sample 290A. In another embodiment, beam generator 210A could produce probe beam 211A as a narrowband beam (e.g., beam generator 210A can comprise a laser) at a desired wavelength. In one embodiment, beam generator 210A can include wavelength adjustment capabilities to allow probe beams 211A with different wavelengths to be directed at test sample 290A during different measurement operations. In another embodiment, metrology system 200A could include multiple beam generators, as indicated by optional beam generator 215A, for directing different probe beams at test sample 290A during sequential or concurrent measurement operations.

Figure 1B:
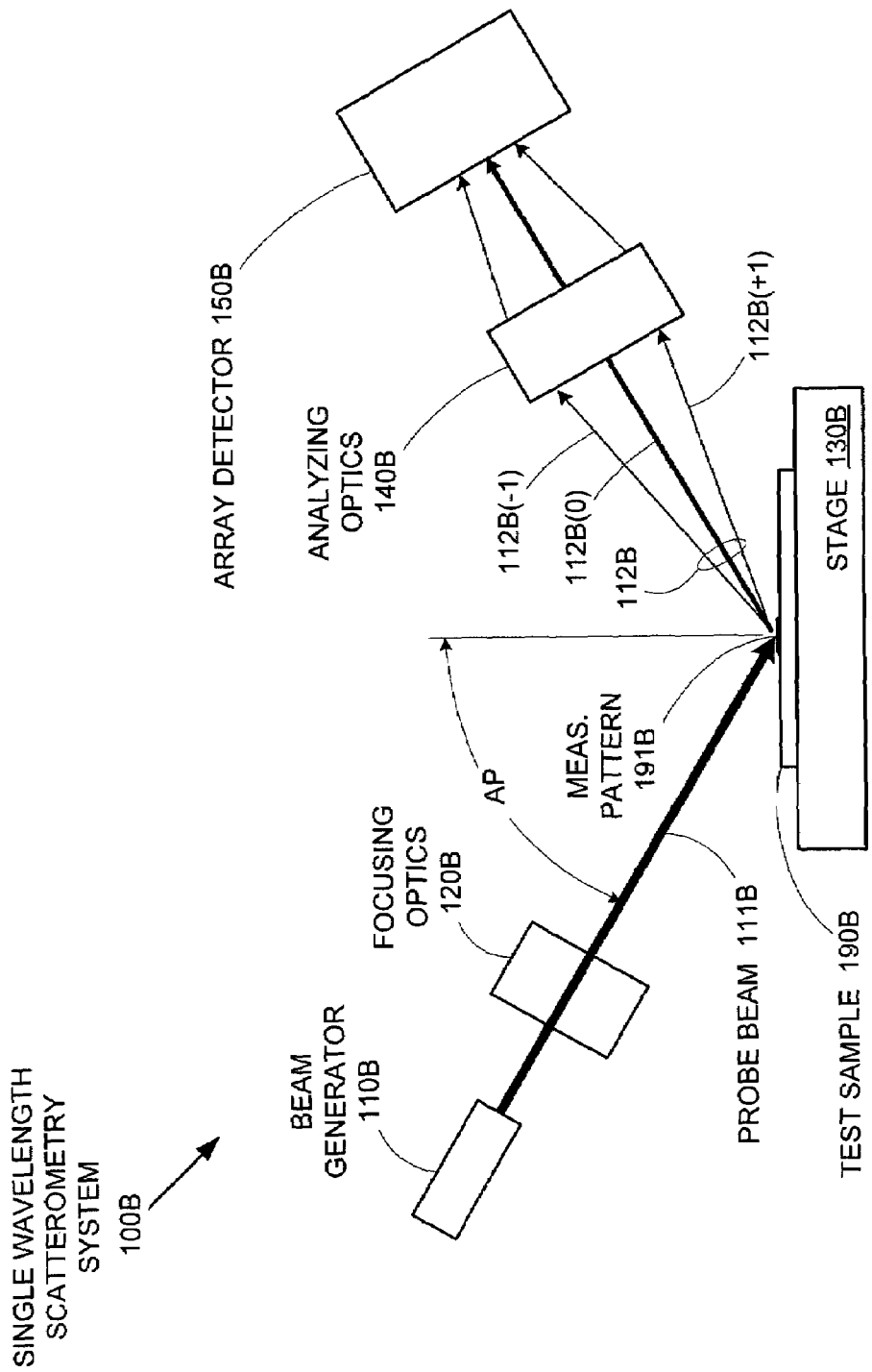

In any case, in response to narrowband probe beam 211A, scattered light 212A is scattered from measurement pattern 291A. The scattered light is collected by analyzing optics 242A. As is known in the art, most of the scattering from measurement pattern 291A will result from elastic (or Rayleigh) scattering, so that most of the light rays in scattered light 212A will have the same wavelength as probe beam 211A. Conventional scatterometry systems (e.g., scatterometry systems 100A and 100B in FIGS. 1A and 1B, respectively) measure and analyze elastically scattered light to determine dimensional information for the measurement pattern.

However, a small portion of scattered light 212A will be due to inelastic scattering, resulting in light rays having wavelengths different than the wavelength of probe beam 211A (e.g., rays 212A(1) and 212A(2)). To prevent the stronger signal from elastically scattered light from overwhelming the measurement of the inelastically scattered light, blocking filter 241A filters out the elastically scattered portions of scattered light 212A while passing the inelastically scattered light 213A (e.g., rays 212A(1) and 212A(2)). The inelastically scattered light is then directed by spectrometer optics 243A onto spectrometer 250A, which disperses the light onto array detector 252A. The spectrum of inelastically scattered light measured by array detector 252A provides a pattern signature for measurement pattern 291A.

Unlike the spectrum of elastically scattered light measured in a conventional scatterometry system (e.g., scatterometry system 100A), the spectrum of inelastically scattered light (e.g., the "Raman spectrum") includes material property information beyond the basic physical characteristics of measurement pattern 291A. This additional material property information is available due to the fact that inelastic scattering occurs when vibrational energy (phonons) from the scattering structures (e.g., measurement pattern 291A) are added to or subtracted from the incident light (e.g., narrowband probe beam 211A). The narrowband probe beam 211A creates a complex array of optical electric fields in measurement pattern 291A, and those optical electric fields add or subtract phonons of specific energies to create inelastically scattered light 212A. The particular phonon energies added to and/or subtracted from the incident light in narrowband probe beam 211A are strongly related to the material properties of the scattering structure (i.e., measurement pattern 291A). For example, the location of one of the peaks in the Raman spectrum is sensitive to the amount of strain in the scattering structure. Therefore, by analyzing the corresponding peak within a Raman spectrum measured by spectrometer 250A, the amount of strain in measurement pattern 291A can be determined.

Note that as the polar angle (i.e., the complement of angle of incidence θ) and/or the azimuthal angle φ between probe beam 211A and measurement pattern 291A change, the distribution of optical electric fields generated in measurement pattern 291A changes, thereby resulting in Raman spectra that emphasize different material properties at different locations within measurement pattern 291A. Therefore, in one embodiment, by measuring Raman spectra at multiple polar and/or azimuthal angles, the material properties at various locations within measurement pattern 291A can be determined. In this manner, the material property distributions (e.g., the strain distribution) within measurement pattern 291A can be measured at subwavelength spatial resolutions, just as standard scatterometry systems can measure subwavelength dimensions. In another embodiment, similar spatial resolution can be achieved by measuring Raman spectra over a range of wavelengths for probe beam 211A (in which case beam generator 210A could be an adjustable wavelength beam generator).

For example, in one embodiment, metrology system 200A can be configured to measure strain in silicon formed over silicon germanium. Because silicon has a smaller lattice size than silicon germanium, a silicon layer formed on top of a silicon germanium layer will exhibit significant induced strain. This strain can actually enhance device performance by improving carrier mobility. Historically, strain has been measured using the micro-Raman techniques, in which the Raman spectrum of a test film is analyzed to determine strain. However, because strain is highly dependent on structure size (e.g., 25 nm and below for advanced semiconductor devices), a strain measurement performed on a bulk film (i.e., a larger film such as a blanket film over an entire wafer) will not match the strain present in an actual device. Unfortunately, because the measurement spot of the highest resolution micro-Raman tools is on the order of 0.5 µm, conventional strain measurement techniques cannot effectively measure strain in modern IC structures.

However, the use of pattern-based Raman spectrum generation, as described above with respect to FIG. 2A, overcomes these limitations of conventional techniques, and enables accurate strain measurements on even the smallest semiconductor structures. For example, beam generator 210A could be an argon ion laser generating a probe beam 211A with a wavelength of 488 nm, and focusing optics 220A could focus probe beam 211A down to a 50 um×50 um spot on measurement pattern 291A In one embodiment, metrology system 200A can include an optional positioning mechanism 216A to allow angle of incidence θ to be scanned between a selected range (e.g., 0° to 70°) while maintaining the spot illuminated by probe beam 211A at the same location on measurement pattern 291A. Note that the specific position and configuration of positioning mechanism 216A is exemplary only, and alternative and/or additional positioning mechanisms (such as steppers, x-y tables, gimbals, goniometers, and any other mechanisms) can be included anywhere within metrology system 200A. For example, stage 230A can include a rotational positioning mechanism 231A for changing the azimuthal angle φ of probe beam 211A relative to measurement pattern 290A. In another embodiment, analyzing optics 240A can include a collection lens for focusing the (filtered) inelastically scattered light 217A onto spectrometer 250A, with the collection lens having a large enough numerical aperture to collect the scattered light from the entire range of angles of incidence θ without moving. The resulting inelastically scattered light data (e.g., Raman spectra) measured by spectrometer 250A could then be used to generate a strain map across measurement pattern 291A, thereby allowing the strain exhibited by individual structures within measurement pattern 291A to be accurately determined.

In another embodiment, focusing optics 220A can include a polarizer and analyzing optics 242A can include an analyzer to allow polarization analysis to be performed on the incoherent inelastically scattered light 217A. Specifically, the polarizer could apply a specific polarization to narrowband probe beam 211A, and the analyzer could enable the change in polarization state exhibited by scattered light 217A.

The actual analysis of the inelastically scattered light data measured by metrology system 200A is performed by computing system 260A. Computing system 260 includes inelastic scatterometry logic 261A for analyzing the measurement data produced by detector 252A. In one embodiment, computing system 260A can also include optional standard scatterometry logic 262A for performing standard scatterometry analyses (e.g., as described with respect to FIG. 1B). Computing system 260A can be any type of system for performing automated data analysis, such as a personal computer or a thin client running off of a network server. Likewise, Inelastic scatterometry logic 261A can be any control logic (e.g., software or hardware logic) for causing computing system 260A to perform the appropriate analysis of the Raman spectra measured by detector 252A.

For example, in one embodiment, inelastic scatterometry logic 261A can perform an iterative operation to determine the material property distribution(s) across measurement pattern 291A. A trial material property distribution is estimated for measurement pattern 291A, and the expected Raman spectra (or any other measurement data for inelastically scattered light 212A) for each angle of incidence (90-θ) and/or azimuthal angle φ and/or wavelength for narrowband probe beam 211A is calculated from a mathematical model of measurement pattern 291A. The actual measured Raman spectra (from spectrometer 250A) are then compared to the expected Raman spectra. Based on the differences between the expected and measured Raman spectra, the trial material property distribution is adjusted to generate a new set of expected Raman spectra to be compared to the measured Raman spectra. This process continues until a desired match is detected between the expected and measured Raman spectra, at which point the trial material property distribution can be provided as the final material property distribution (i.e., the measurement result of the scatterometry process).

Figure 2B:
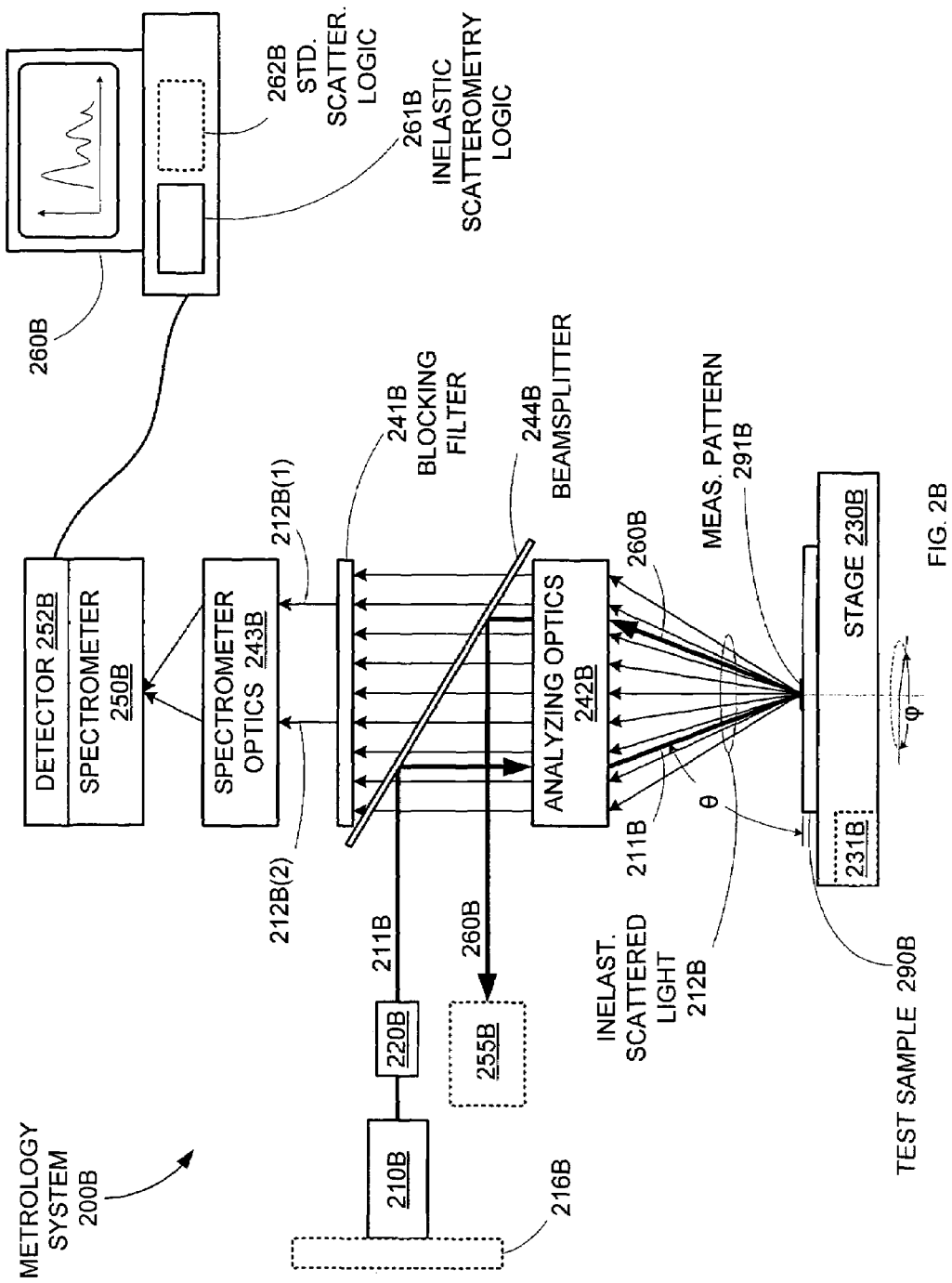

FIG. 2B shows another embodiment of a metrology system 200B that incorporates capabilities for analyzing incoherent inelastic scattering from a sample pattern. Metrology system 200B is substantially similar to (and operates in a manner substantially similar to) metrology system 200A shown in FIG. 2A, except that probe beam directional control is provided by a beamsplitter 244B. In addition to beamsplitter 244B, Metrology system 200B also includes a narrowband beam generator 210B, focusing optics 220B, a stage 230B for supporting a test sample 290B, a blocking filter 241B, analyzing optics 242B, spectrometer optics 243B, a spectrometer 250B, and an array detector 252B. A computing system 260B can be coupled to or incorporated into metrology system 200B to perform analysis on the data gathered by spectrometer 250B. In various embodiments, metrology system 200B can also include multiple sensors to provide additional metrology capabilities, as indicated by optional sensor 255B. Sensor 255B can represent any type and number of detection elements (and associated optics), such as an additional spectrometer, an intensity detector, or an array detector, among others. For example, in one embodiment, sensor 255B could be an array detector, thereby providing metrology system 200B with standard scatterometry capabilities (e.g., as described with respect to FIGS. 1A and/or 1B).

To perform a measurement operation, beam generator 210B generates a narrowband probe beam 211B that is directed onto a measurement pattern 291B on test sample 290B by means of beamsplitter 244B and analyzing optics 242B. The incoherent inelastically scattered light 212B generated in response to probe beam 211B is collected by analyzing optics 242B, passes through beamsplitter 244B, and is filtered by blocking filter 241B. The elastically scattered light rays do not pass through blocking filter 241B, while the incoherent inelastically scattered light rays 212B(1) and 212B(2) pass through blocking filter 241B and are focused onto spectrometer 250B by spectrometer optics 243B. The polar angle (i.e., the complement of angle of incidence θ) of probe beam 211B can be adjusted by moving beam generator 210B and focusing optics 220B vertically (for example using optional positioning mechanism 216B), while the azimuthal angle of measurement pattern 291B can be adjusted using optional rotational positioning mechanism 231B in stage 230B. Furthermore, just as described with respect to FIG. 2A, beam generator 210B can include the capability to generate narrowband probe beam 211B over a range of wavelengths.

Once a set of inelastically scattered light data (e.g., Raman spectra) has been measured by detector 252B for a variety of polar and/or azimuthal angles and/or probe beam wavelengths, inelastic scatterometry logic 261B (e.g., software or hardware logic) in computing system 260B (e.g., a personal computer, server, or embedded computing resources) can analyze that data in substantially the same manner as described with respect to computing system 260A in FIG. 2A to generate material property data for measurement pattern 291B.

Note that in one embodiment, computing system 260B can also include optional standard scatterometry logic 262B for performing standard scatterometry analyses on data gathered by optional detector 255B. For example, elastically diffracted light 260B, which is generated in response to probe beam 211B at the same time that inelastically scattered light 212B is generated and which includes of one or more diffracted orders, can be directed by analyzing optics 242B and beamsplitter 244B onto optional detector 255B. Detector 255B may consist of any number of optical elements and detectors necessary to perform an elastic scatterometry analysis on diffracted light 260B (as described with respect to FIG. 1B). Optional detector 255B may also be moved vertically or may have a large enough aperture to collect elastic light at a range of polar angles without adjustment.

Note further that any type of incoherent inelastic scattering process(es) can be used by metrology systems 200A and 200B to generate inelastically scattered light 212A and 212B, respectively, for the measurement of material properties. Some of these processes are photoluminescence, fluorescence, phosphorescence, Brillouin scattering, as well as others. For example, photoluminescence involves the use of a narrowband probe beam to create electron-hole pairs in silicon or silicon germanium. The electron-hole pairs recombine and create incoherent light with a range of wavelengths longer than the probe beam. The photoluminescence spectrum can then be used as a measure of crystal dislocations and defects in the silicon or silicon germanium.

Note further that in addition to incoherent inelastic scattering processes, coherent inelastic scattering processes also exist that may be used to generate the inelastically scattered light for use in a scatterometry analysis to determine material properties. For example, one such process is second harmonic generation, which occurs when an intense narrowband probe beam is incident upon the surface of a material and generates an output beam with a wavelength exactly half the probe wavelength. It is preferable for the source of the probe beam to be a pulsed laser with a large peak power for best efficiency of second harmonic generation. In the past, second harmonic generation has been used to determine electric fields and trapped charge at the surface of relatively large silicon and silicon germanium structures.

Figure 2C:
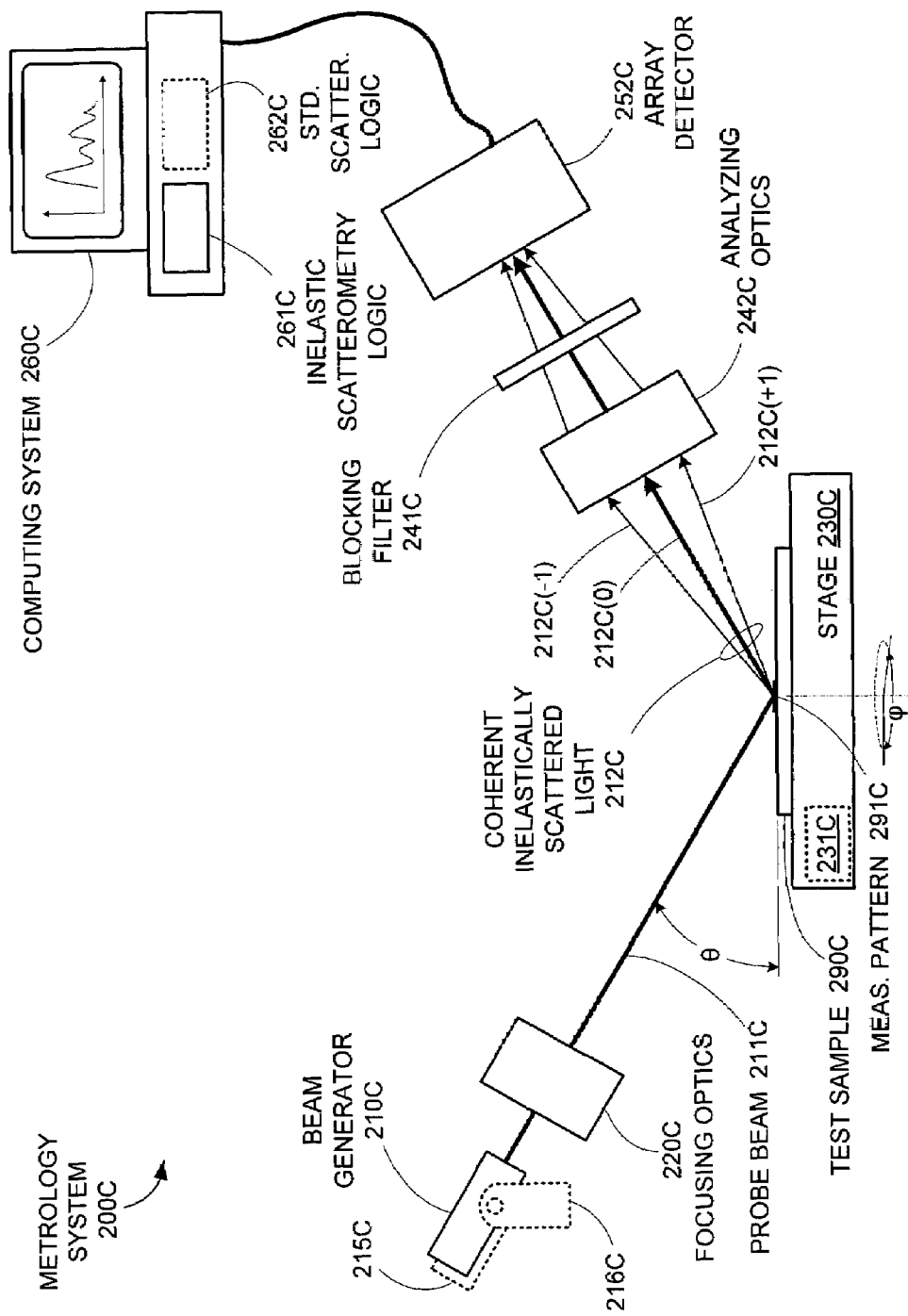
FIG. 2C is a diagram of a metrology system based on coherent inelastic scattering from a measurement pattern.

FIG. 2C is an embodiment of a metrology system 200C for generating material property measurements based on coherent inelastic scattering from sample patterns. Metrology system 200C includes a beam generator 210C, focusing optics 220C, a stage 230C for supporting a test sample 290C, analyzing optics 242C, a blocking filter 241C, an array detector 252C, and a computing system 260C. To perform a measurement operation, beam generator 210C generates an intense narrowband probe beam 211C that is directed onto a measurement pattern 291C on test sample 290C by focusing optics 220C. The coherent inelastically scattered light 212C is collected by analyzing optics 242C, and is then passed through blocking filter 241C to filter out any elastically scattered light. The coherent inelastically scattered light passes through the filter and is detected by detector 252C.

In one embodiment, detector 252C can be an array detector to measure the spatial distribution of multiple diffracted orders (e.g., as indicated by negative first order beam 212C(−1), zeroth order beam 212C(0), and first order beam 212C(+1)), or may be a single intensity detector for a single order. The measurements may be taken at multiple wavelengths by adjusting the wavelength of the beam generator 210C (or by using additional optional beam generators 215C), and/or may be taken at multiple polar angles by adjusting the position of source 210C relative to stage 230C (e.g., via optional positioning mechanism 216C), and/or may be taken at multiple azimuthal angles by rotating test sample 290C in its own plane (e.g., via optional rotational mechanism 231C in stage 230C).

Once a number of measurements have been taken for a range of polar and/or azimuthal angles and/or probe beam wavelengths, inelastic scatterometry logic 261C (e.g., software or hardware logic) in computing system 260C (e.g., a personal computer, server, or embedded computing resources) can analyze those spectra in substantially the same manner as described with respect to computing system 260A in FIG. 2A to generate material property data for measurement pattern 291C. Note that like computing system 260A, computing system 260C can include optional standard scatterometry logic 262C for performing standard scatterometry analyses.

Note further that coherent inelastically scattered light 212C can include diffraction orders not present in incoherent inelastically scattered light. Therefore, in addition to logic substantially similar to that present in inelastic scatterometry logic 261A, inelastic scatterometry logic 261C can also include logic for analyzing the angular and intensity arrangement of those diffraction orders in coherent inelastically scattered light 212C to extract additional information about measurement pattern 291C.

Note further that any type of coherent inelastic scattering process(es) can be used by metrology system 200C to generate inelastically scattered light 212C. For example, other techniques for generating coherent inelastically scattered light include third harmonic generation, optical mixing, 4-wave mixing, CARS (coherent anti-Stokes Raman scattering), and stimulated Raman scattering, among others.

Figure 3A:
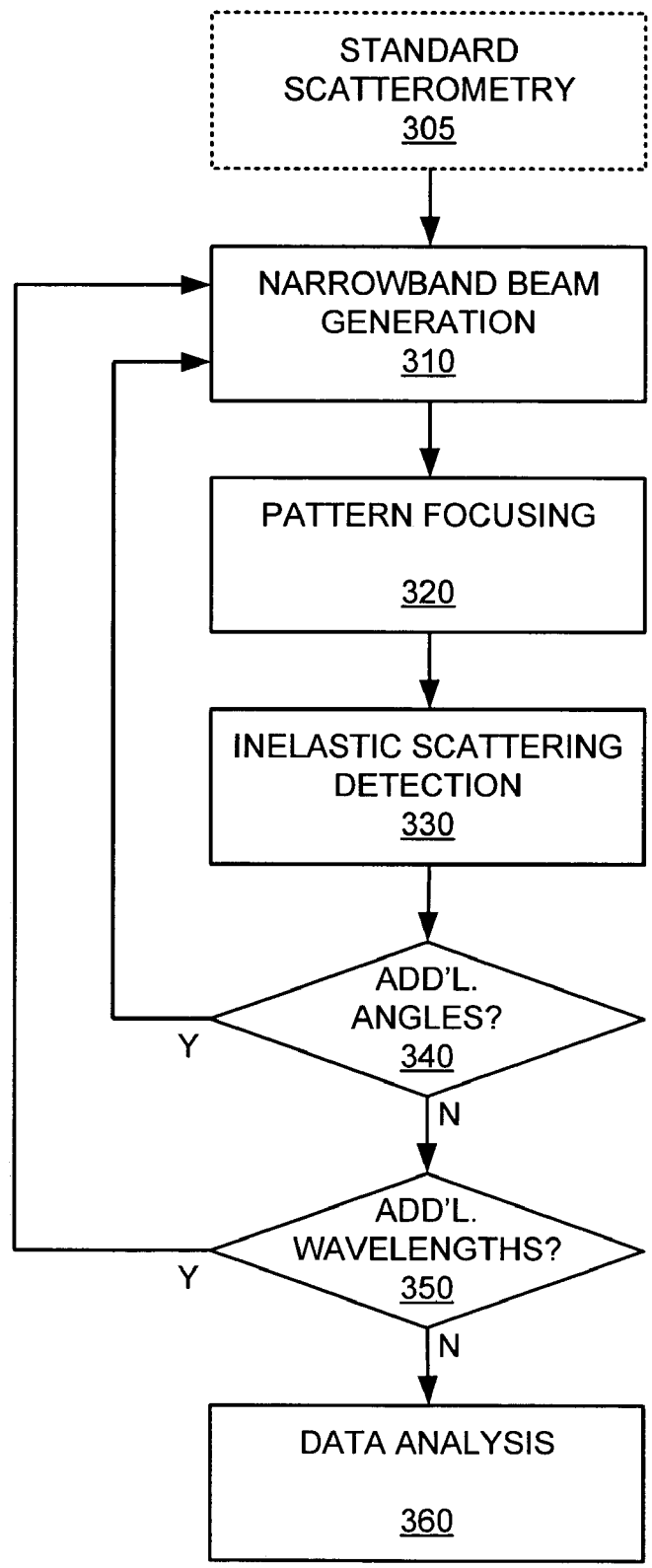
FIGS. 3A and 3B are flow diagrams of a method for performing scatterometry based on inelastically scattered light.

FIG. 3A shows a flow diagram of the metrology operation described with respect to FIGS. 2A, 2B, and 2C. First, in an optional "STANDARD SCATTEROMETRY" step 305, a standard scatterometry operation can be performed (e.g., as described with respect to FIGS. 1A and 1B) to determine physical dimensions of the measurement pattern (291A, 291B, and 291C in FIGS. 2A, 2B, and 2C, respectively) on the test sample (290A, 290B, and 290C in FIGS. 2A, 2B, and 2C, respectively). This physical dimension data can then be used during subsequent data analysis, as described in greater detail below. Note that while step 305 is depicted at the start of the flow diagram for exemplary purposes, in various other embodiments, step 305 can be performed at any point prior to the final data analysis (i.e., step 360).

In a "NARROWBAND BEAM GENERATION" step 310, a narrowband probe beam (e.g., probe beams 211A, 211B, and 211C in FIGS. 2A, 2B, and 2C, respectively) is generated. Then, in a "PATTERN FOCUSING" step 320, the narrowband probe beam is directed onto the measurement pattern in the test sample. The resulting inelastically scattered light (e.g., inelastically scattered light 212A, 212B, and 212C in FIGS. 2A, 2B, and 2C, respectively) is then directed onto a sensor (e.g., spectrometer 250A and detector 252A in FIG. 2A, spectrometer 250B and detector 252B in FIG. 2B, and array detector 252C in FIG. 2C) and measured in an "INELASTIC SCATTERING DETECTION" step 330. If measurements are to be taken at additional polar and/or azimuthal angles for the probe beam, an "ADDITIONAL ANGLES?" step 340 can loop the process back to step 310. Similarly, if measurements are to be taken using probe beams having different wavelengths, an "ADDITIONAL WAVELENGTHS?" step 350 can also loop the process back to step 310. Once all the various measurement conditions have been satisfied, the measured inelastically scattered light data (e.g., Raman spectra) can be analyzed in a "DATA ANALYSIS" step 360 to determine a material property distribution(s) for the measurement pattern (e.g., stress distribution, dopant concentration distribution, crystallinity distribution, charge distribution).

Figure 3B:
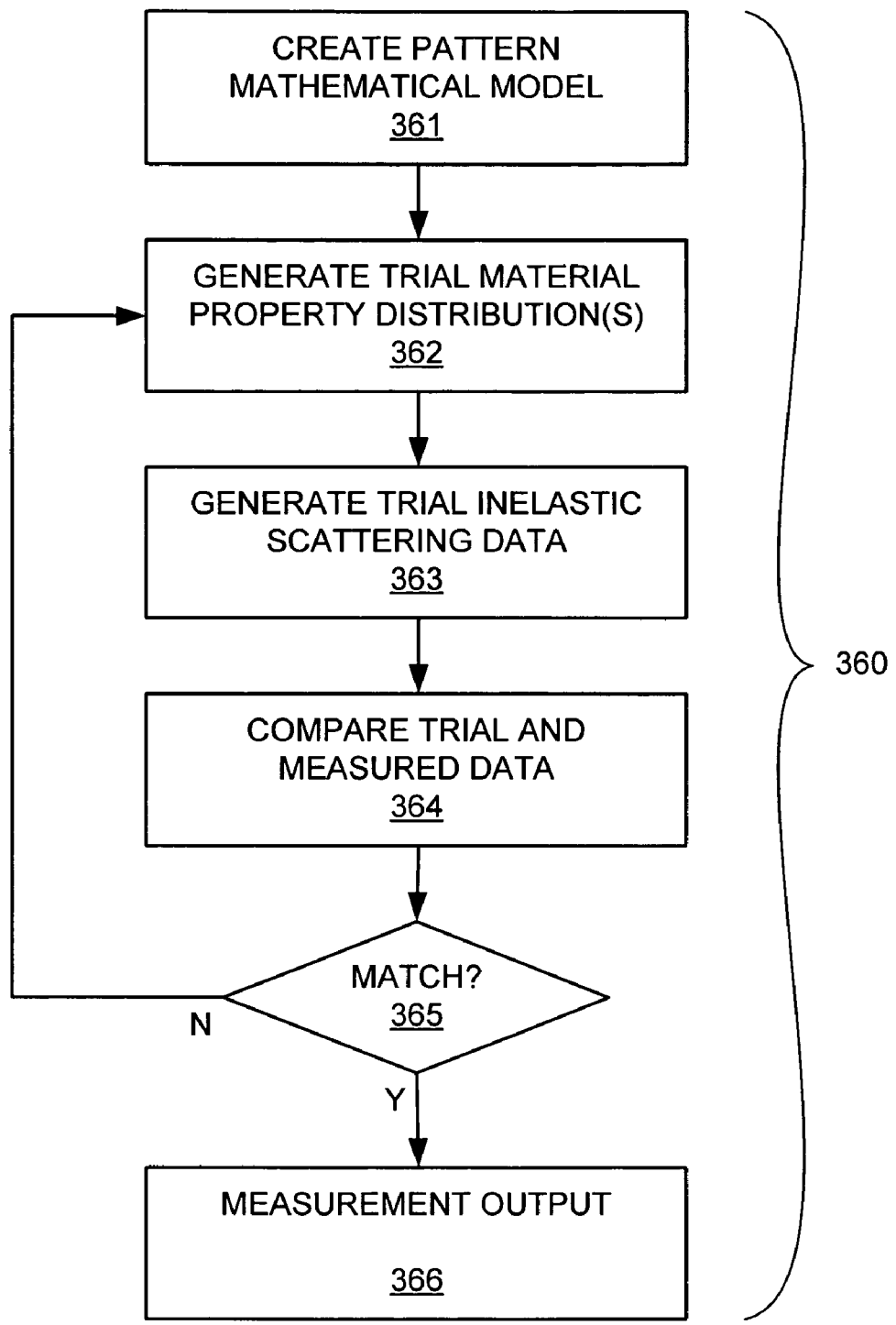

FIG. 3B shows a flow diagram of an embodiment of a data analysis process for the measured inelastically scattered light data gathered in steps 310-350. In a "CREATE PATTERN MATHEMATICAL MODEL" step 361, a mathematical model is generated for the optical behavior of the measurement pattern. Note that the mathematical model can incorporate the dimensional data generated by standard scatterometry in optional step 305 (described above with respect to FIG. 3A). Then, in a "GENERATE TRIAL MATERIAL PROPERTY DISTRIBUTION(S)" step 362, a trial set of material property data is specified for the measurement pattern. The mathematical model is then used to generate a set of expected inelastically scattered light data (e.g., Raman spectra) using the trial material property distribution(s) in a "GENERATE TRIAL INELASTIC SCATTERING DATA" step 363. The expected data is compared to the measured data, and if a match (to a desired tolerance) is not detected in a "MATCH?" step 365, the process loops back to step 362, where the trial material property distribution is modified, and a new set of trial data is generated in step 363 for comparison against the measured data in step 364. The process continues to loop in this manner until a match between the measured and expected data is detected in step 365, at which point the trial material property distribution(s) can be presented as the measurement output in a "MEASUREMENT OUTPUT" step 366.

The various embodiments of the structures and methods of this invention that are described above are illustrative only of the principles of this invention and are not intended to limit the scope of the invention to the particular embodiments described. Thus, the invention is limited only by the following claims and their equivalents.

The invention claimed is:

1. A metrology system comprising:
a narrowband beam generation system for directing a narrowband probe beam at a measurement pattern on a test sample;
a first sensor;
a set of output optics for directing inelastically scattered light from the measurement pattern in response to the narrowband probe beam onto the first sensor; and
a computing system for performing a scatterometry analysis on inelastically scattered light data measured by the first sensor, wherein the computing system comprises:
means for generating a set of trial inelastically scattered light data by applying a trial distribution for a material property of the measurement pattern to a mathematical model of the measurement pattern;
means for comparing the set of trial inelastically scattered light data to a set of measured inelastically scattered light data for the measurement pattern measured by the first sensor;
means for adjusting the trial distribution until the set of trial inelastically scattered light data matches the set of measured inelastically scattered light data; and
means for providing the trial distribution as an output distribution of the material property for the measurement pattern when the set of trial inelastically scattered light data matches the set of measured inelastically scattered light data to within a specified tolerance.

2. The metrology system of claim 1, wherein the narrowband beam generation system comprises:
a laser for generating the narrowband probe beam; and
focusing optics for directing the narrowband probe beam onto the measurement pattern.

3. The metrology system of claim 1, further comprising an adjustment mechanism for changing an angle of incidence between the narrowband probe beam and the test sample.

4. The metrology system of claim 1, further comprising an adjustment mechanism for changing an azimuthal angle between the narrowband probe beam and the measurement pattern.

5. The metrology system of claim 1, wherein the narrowband beam generation system comprises an adjustable beam generator for adjusting a wavelength of the narrowband probe beam.

6. The metrology system of claim 1, further comprising a second sensor for measuring elastically scattered light from the measurement pattern, wherein the computing system further comprises:
    means for generating dimensional information for the measurement pattern by performing a scatterometry analysis on elastically scattered light data for the measurement pattern measured by the second sensor; and
    means for generating the mathematical model using the dimensional information.

7. The metrology system of claim 1, wherein the first sensor comprises an array detector, and
    wherein the inelastically scattered light comprises coherent inelastically scattered light.

8. The metrology system of claim 1, wherein the set of output optics comprises a blocking filter for blocking elastically scattered light from the measurement pattern from reaching the spectrometer.

9. The metrology system of claim 1, wherein the first sensor comprises a spectrometer, and
    wherein the inelastically scattered light comprises incoherent inelastically scattered light.

10. The metrology system of claim 8, wherein the narrowband beam generation system comprises a polarizer for polarizing the narrowband probe beam, and
    wherein the set of output optics further comprises an analyzer for measuring a polarization state of the inelastically scattered light.

11. The metrology system of claim 9, further comprising:
    a second sensor; and
    a beam splitter for directing the first narrowband probe beam towards the measurement pattern and for directing elastically scattered light from the measurement pattern at the second sensor.

12. A method for analyzing a semiconductor wafer, the method comprising:
    generating a first set of inelastically scattered light from a measurement pattern on the semiconductor wafer;
    measuring a first set of inelastic scattering data for the first set of inelastically scattered light; and
    determining a distribution for at least one material property in the measurement pattern by analyzing the first set of inelastic scattering data, wherein determining the distribution comprises:
        generating a set of trial inelastic scattering data by applying a trial distribution for the at least one material property in the measurement pattern to a mathematical model of the measurement pattern;
        comparing the set of trial inelastic scattering data to the first set of inelastic scattering data;
        adjusting the trial distribution until the set of trial inelastic scattering data matches the first set of inelastic scattering data to within a specified tolerance; and
        providing the trial distribution as the distribution of the at least one material property for the measurement pattern when the set of trial inelastic scattering data matches the first set of inelastic scattering data to within the specified tolerance.

13. The method of claim 12, wherein measuring the first set of inelastic scattering data comprises measuring coherent inelastically scattered light in the first set of inelastically scattered light using an array detector.

14. The method of claim 12, further comprising:
    generating a set of elastically scattered light from the measurement pattern;
    measuring a set of elastic scattering data for the set of elastically scattered light;
    performing a scatterometry analysis on the set of elastic scattering data to determine a set of physical characteristics for the measurement pattern; and
    generating the mathematical model using the set of physical characteristics.

15. The method of claim 12, wherein the measurement pattern is dimensionally similar to functional devices on the semiconductor wafer, the method further comprising extracting a set of values for the at least one material property for the functional devices from the distribution of the at least one material property for the measurement pattern.

16. The method of claim 12 wherein the measurement property is one of stress, strain, embedded charge, composition and degree of crystallinity.

17. The method of claim 12, further comprising:
    generating a second set of inelastically scattered light from the measurement pattern; and
    measuring a second set of inelastic scattering data for the second set of inelastically scattered light,
    wherein determining the distribution further comprises analyzing the second set of inelastic scattering data.

18. The method of claim 12, wherein measuring the first set of inelastic scattering data comprises measuring incoherent inelastically scattered light in the first set of inelastically scattered light using a spectrometer.

19. The method of claim 17, wherein generating the first set of inelastically scattered light comprises directing first narrowband probe beam at the measurement pattern, the first narrowband probe beam having a first polar angle relative to the semiconductor wafer, a first azimuthal angle relative to the first measurement pattern, and a first wavelength,
    wherein generating the second set of inelastically scattered light comprises directing a second narrowband probe beam at the measurement pattern, the second narrowband probe beam having a second polar angle between relative to the semiconductor wafer, a second azimuthal angle relative to the measurement pattern, and a second wavelength, and
    wherein at least one of the second polar angle, the second azimuthal angle, and the second wavelength is different from the first polar angle, the first azimuthal angle, and the first wavelength, respectively.

20. The method of claim 18, wherein the first set of inelastic scattering data comprises a Raman spectrum.

* * * * *